United States Patent
Lei et al.

(10) Patent No.: US 9,643,904 B2
(45) Date of Patent: May 9, 2017

(54) METHOD FOR PREPARING 2,3,3,3-TETRAFLUOROPROPENE

(71) Applicants: Zhejiang Quzhou Juxin Fluorine Chemical Co., Ltd., Quzhou (CN); Zhejiang Quhua Fluor-Chemistry Co., Ltd., Quzhou (CN)

(72) Inventors: Jun Lei, Ningbo (CN); Aiguo Wang, Quzhou (CN); Bo Yang, Quzhou (CN); Yan Zhang, Quzhou (CN); Huadong Zhou, Quzhou (CN); Yang Zhao, Quzhou (CN); Yi Zhu, Quzhou (CN); Haili Xia, Quzhou (CN); Haojin Shi, Quzhou (CN)

(73) Assignees: ZHEJIANG QUZHOU JUXIN FLUORINE CHEMICAL CO., LTD., Quzhou (CN); ZHEJIANG QUHUA FLUOR-CHEMISTRY CO., LTD., Quzhou (CN)

( * ) Notice: Subject to any disclaimer, the term of this patent is extended or adjusted under 35 U.S.C. 154(b) by 0 days.

(21) Appl. No.: 15/378,019

(22) Filed: Dec. 13, 2016

(65) Prior Publication Data

US 2017/0088493 A1    Mar. 30, 2017

Related U.S. Application Data

(63) Continuation-in-part of application No. PCT/CN2015/000655, filed on Sep. 21, 2015.

(30) Foreign Application Priority Data

Jul. 30, 2015   (CN) .......................... 2015 1 0459642

(51) Int. Cl.
  *C07C 17/23*   (2006.01)
  *C07C 17/383*  (2006.01)

(52) U.S. Cl.
  CPC ............ *C07C 17/23* (2013.01); *C07C 17/383* (2013.01)

(58) Field of Classification Search
  CPC .............................. C07C 17/23; C07C 17/383
  See application file for complete search history.

(56) References Cited

U.S. PATENT DOCUMENTS

2011/0112338 A1*  5/2011  Smith ..................... C07C 17/25
                                                                570/153

* cited by examiner

*Primary Examiner* — Jafar Parsa
(74) *Attorney, Agent, or Firm* — Matthias Scholl, PC; Matthias Scholl

(57) ABSTRACT

A method for preparing 2,3,3,3-tetrafluoropropene, including: a) introducing hexafluoropropylene and hydrogen to a first reactor for reaction in the presence of a catalyst to obtain a first mixture; b) washing and drying the first mixture, and introducing the treated first mixture to a first distillation column to obtain 1,1,1,2,3,3-hexafluoropropane, 1,1,1,2,3-pentafluoropropene, and hexafluoropropylene; recycling the 1,1,1,2,3,3-hexafluoropropane to the first reactor, and introducing the 1,1,1,2,3-pentafluoropropene and the hexafluoropropylene to a second distillation column to yield hexafluoropropylene and 1,1,1,2,3-pentafluoropropene; and recycling the hexafluoropropylene to the first reactor; c) introducing the 1,1,1,2,3-pentafluoropropene and hydrogen to a second reactor in the presence of a catalyst to obtain a second mixture; and d) washing and drying the second mixture, and introducing the second mixture to a third distillation column to yield 1,1,1,2,3-pentafluoropropane; and recycling the 1,1,1,2,3-pentafluoropropane to the second reactor to yield 2,3,3,3-tetrafluoropropene.

6 Claims, 1 Drawing Sheet

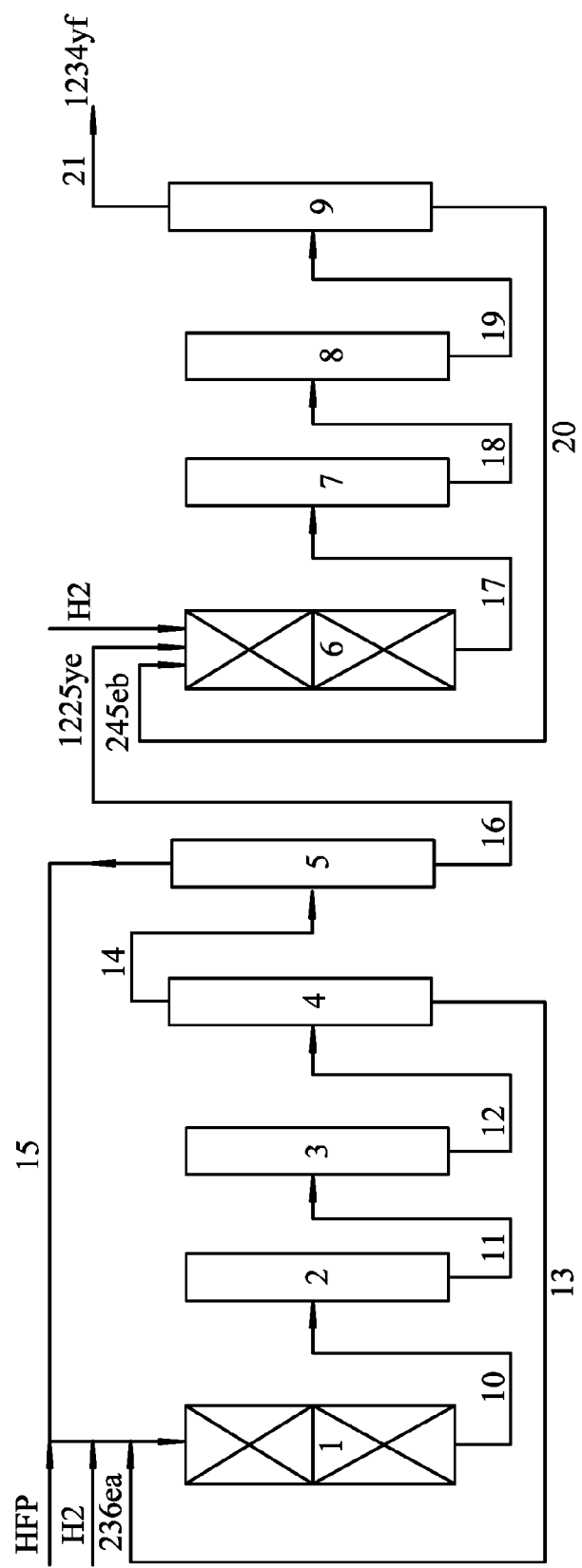

METHOD FOR PREPARING 2,3,3,3-TETRAFLUOROPROPENE

CROSS-REFERENCE TO RELATED APPLICATIONS

This application is a continuation-in-part of International Patent Application No. PCT/CN2015/000655 with an international filing date of Sep. 21, 2015, designating the United States, now pending, and further claims foreign priority benefits to Chinese Patent Application No. 201510459642.2 filed Jul. 30, 2015. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND OF THE INVENTION

Field of the Invention

The invention relates to a method for preparing 2,3,3,3-tetrafluoropropene.

Description of the Related Art

A conventional method for preparing 2,3,3,3-tetrafluoropropene utilizes hexafluoropropylene (HFP) and hydrogen as raw materials and involves a four-step process, including a two-step hydrogenation and a two-step dehydrofluorination. Thus, the conventional method is long, inefficient, and costly.

SUMMARY OF THE INVENTION

In view of the above-described problems, it is one objective of the invention to provide a method for preparing 2,3,3,3-tetrafluoropropene that is shorter, more efficient, and less expensive, and produces the desired material with more selectivity and in greater yield.

To achieve the above objective, in accordance with one embodiment of the invention, there is provided a method for preparing 2,3,3,3-tetrafluoropropene. The method comprises:

a) introducing hexafluoropropylene and hydrogen to a first reactor to allow hexafluoropropylene to react with hydrogen in the presence of a catalyst to obtain a first mixture comprising 1,1,1,2,3-pentafluoropropene, 1,1,1,2,3,3-hexafluoropropane, hydrogen fluoride, and hexafluoropropylene, in which, a molar ratio of hexafluoropropylene to hydrogen is between 1:0.95 and 1:0.99, a space velocity is between 200 and 1000 $h^{-1}$, a reaction temperature is between 50 and 400° C.;

b) washing and drying the first mixture obtained from a), and introducing the treated first mixture to a first distillation column to obtain 1,1,1,2,3,3-hexafluoropropane in a bottom of the first distillation column and 1,1,1,2,3-pentafluoropropene and hexafluoropropylene at a top thereof; recycling 1,1,1,2,3,3-hexafluoropropane to the first reactor, and introducing 1,1,1,2,3-pentafluoropropene and hexafluoropropylene to a second distillation column to yield hexafluoropropylene at a top of the second distillation column and 1,1,1,2,3-pentafluoropropene at a bottom thereof; recycling hexafluoropropylene to the first reactor;

c) introducing 1,1,1,2,3-pentafluoropropene obtained from b) and hydrogen to a second reactor and allowing 1,1,1,2,3-pentafluoropropene to react with hydrogen in the presence of a catalyst, to obtain a second mixture comprising 1,1,1,2,3-pentafluoropropane, 2,3,3,3-tetrafluoropropene, HF, and $H_2$, in which a molar ratio of hydrogen to 1,1,1,2,3-pentafluoropropene is between 1:0.95 and 1:0.99, a space velocity is between 300 and 2000 $h^{-1}$, and a reaction temperature is between 80 and 500° C.; and d) washing and drying the second mixture obtained from c), and introducing the second mixture to a third distillation column to yield 1,1,1,2,3-pentafluoropropane at a bottom thereof; and recycling 1,1,1,2,3-pentafluoropropane to the second reactor, to yield 2,3,3,3-tetrafluoropropene at a top thereof.

In a class of this embodiment, the space velocity in a) is between 400 and 800 $h^{-1}$, and the reaction temperature is between 100 and 300° C.

In a class of this embodiment, the space velocity in c) is between 600 and 1500 $h^{-1}$, and the reaction temperature is between 120 and 400° C.

In a class of this embodiment, the catalyst in the first reactor is respectively filled in an upper section and a lower section of the first reactor. The catalyst in the upper section of the first reactor is Pd/C, and Pd accounts for between 0.1 and 1 wt. %. The catalyst in the lower section of the first reactor is chromium oxide.

In a class of this embodiment, the catalyst in the second reactor is respectively filled in an upper section and a lower section of the second reactor. The catalyst in the upper section of the second reactor is $Pd/Al_2O_3$, and Pd accounts for between 0.2 and 1.5 wt. %. The catalyst in the lower section of the second reactor comprise between 80 and 90 wt. % of chromium oxide and between 10 and 20 wt. % of zinc oxide.

In a class of this embodiment, both the first reactor and the second reactor are adiabatic reactors.

Both the first reactor and the second reactor can be divided into two sections with each section filled with different catalysts. The raw materials hexafluoropropylene and $H_2$ after being heated by a preheater enter the first reactor for reaction under the action of the catalysts in the upper section and the lower section. The dose of hexafluoropropylene is slightly excessive while $H_2$ is completely converted, thus, an obtained mixture includes 1,1,1,2,3,3-hexafluoropropane produced from the reaction, and a small amount of non-reacted hexafluoropropylene. The mixture then enters the lower section of the reactor where dehydrofluorination of 1,1,1,2,3,3-hexafluoropropane in a gas phase is performed to yield a mixture including 1,1,1,2,3,3-hexafluoropropane, 1,1,1,2,3-pentafluoropropene, HF, and a small amount of hexafluoropropylene. The mixture is then separated, the non-reacted 1,1,1,2,3,3-hexafluoropropane and hexafluoropropylene are returned to the first reactor, and 1,1,1,2,3-pentafluoropropene and the fresh $H_2$ are preheated by a preheater and introduced to the second reactor for reaction under the action of the catalysts of the upper and the lower sections, during which, the dose of $H_2$ is slightly excessive and 1,1,1,2,3-pentafluoropropene is completely converted, a resulting mixture includes 2,3,3,3-tetrafluoropropene, 1,1,1,2,3-pentafluoropropane, HF, and a small amount of $H_2$. The mixture is then separated to yield the product 2,3,3,3-tetrafluoropropene, while the non-reacted 1,1,1,2,3-pentafluoropropane is returned to the second reactor and the small amount of $H_2$ is discharged.

Hydrogenation of hexafluoropropylene and dehydrofluorination of 1,1,1,2,3,3-hexafluoropropane are performed in the first reactor. The hydrogenation of hexafluoropropylene is a strong exothermic reaction. The activity of the catalyst and the selectivity of the products are greatly influenced by the reaction temperature, and too high the temperature may result in coking and deactivation of the catalyst for hydrogenation. The temperature of the hydrogenation is lower than the temperature of dehydrofluorination, the heat quantity of the lower section is partially supply of heat quantity produced by the hydrogenation of the upper section, and the heat quantity of the hydrogenation of the upper section is carried away by the excessive 1,1,1,2,3,3-hexafluoropropane. The temperature of the upper section of the first reactor is controlled between 50 and 150° C., and preferably between 80 and 120° C., and the temperature of the lower section is between 250 and 400° C. The higher the space velocity is, the more the materials that the unit catalyst surface contacts are, and the higher the loading of the reaction is. Thus, based on comprehensive consideration, the selected space velocity is between 200 and 1000 $h^{-1}$, preferably between 400 and 800 $h^{-1}$. To make $H_2$ totally converted for avoiding subsequent separation problem of $H_2$, the dose of hexafluoropropylene is slightly excessive and the excessive hexafluoropropylene can be returned to the first reactor; and the molar ratio of hexafluoropropylene to hydrogen is between 1:0.95 and 1:0.99.

Hydrogenation of 1,1,1,2,3-pentafluoropropene and dehydrofluorination of 1,1,1,2,3-pentafluoropropane are performed in the second reactor. Similar to the reactions in the first reactor, a part of the heat quantity of the lower section is also supplied by the heat quantity produced in the hydrogenation in the upper section. 1,1,1,2,3-pentafluoropropene is made completely converted, thus avoiding the subsequent problems of difficult separation of 1,1,1,2,3-pentafluoropropene and 2,3,3,3-tetrafluoropropene. The temperature of the upper section of the second first reactors controlled between 80 and 200° C., preferably between 100 and 150° C., and the temperature of the lower section is controlled at between 300 and 500° C., and the space velocity is controlled between 300 and 2000 $h^{-1}$, preferably between 600 and 1500 $h^{-1}$, and a molar ratio of $H_2$ to 1,1,1,2,3-pentafluoropropene is between 1:0.95 and 1:0.99.

The upper sections of the first reactor and the second reactor are filled with the precious metal Pd catalyst. As the loading amount of the precious metal is too low, the catalytic activity is not enough, and a best balance point exists among the amount of Pd and the catalytic activity. The selection of the carrier is critical for the catalyst. The hydrogenation of HFP is easily carried out, the activated carbon is selected as the catalyst because of its high specific area, which is beneficial to load catalytic substance with small amount but high dispersion degree and to prepare catalyst of high catalytic activity. The hydrogenation of 1,1,1,2,3-pentafluoropropene is difficult, the $Al_2O_3$ carrier has relatively strong acidity, the active component Pd is well dispersed on the carrier. $Al_2O_3$ carrier has high mechanical strength, and the catalyst has long service life. It is found from the experiment that the upper section of the first reactor is filled with the Pd/C catalyst and Pd accounts for between 0.1 and 1 wt. %, and the lower section of the second first reactors filled with the Pd/$Al_2O_3$ catalyst and Pd accounts for between 0.2 and 1.5 wt. %. Pretreatment of the catalyst can be conducted in other reactors.

The catalysts in the lower sections of the first reactor and the second reactor are those including chromium oxide as the active component. The catalyst of the lower section of the first reactor is the pure chromium oxide, and the catalyst of the lower section of the second reactor comprises between 80 and 90 wt. % of chromium oxide and between 10 and 20 wt. % of zinc oxide and is prepared as follows: mixing nitrates of chromium and zinc according to a certain ratio to prepare a diluted solution of a certain concentration, adding a precipitant for reaction, performing filtration, washing by water, desiccation, calcination, granulation, and tablet pressing to prepare a precursor, fluorinating the precursor to yield the catalyst. The pretreatment of the catalyst can be conducted in other reactors.

Both the first reactor and the second reactor adopt the adiabatic type or the isothermal type, preferably adopting the adiabatic type. And the material of the reactors can adopt the carbon steel or the stainless steel.

Advantages of a method for preparing 2,3,3,3-tetrafluoropropene according to embodiments of the invention are summarized as follows:

1. The two-step gas phase route is adopted, the procedure is simple, and there are few byproducts produced.
2. The conversion rate and the selectivity are high, the conversion rate of hexafluoropropylene is higher than 99%, and the conversion rate of 1,1,1,2,3-pentafluoropropene is 100%. Both the selectivity of 1,1,1,2,3,3-hexafluoropropane and 1,1,1,2,3-pentafluoropropane are 100%.
3. $H_2$ of the first reactor is totally converted and 1,1,1,2,3-pentafluoropropene of the second first reactors totally converted, so that the separation problems of the non-reacted $H_2$ and 1,1,1,2,3-pentafluoropropene are solved.
4. The heat quantity produced in the hydrogenation is fully utilized by the dehydrofluorination, thus, the heat quantity is comprehensively utilized, and the energy consumption is reduced.

BRIEF DESCRIPTION OF THE DRAWINGS

The invention is described hereinbelow with reference to accompanying drawings, in which the sole FIGURE is a flow chart illustrating a method for preparing 2,3,3,3-tetrafluoropropene according to one embodiment of the invention.

In the drawings, the following reference numbers are used: 1. First reactor; 2. First alkaline washing column; 3. First drying column; 4. First distillation column; 5. Second distillation column; 6. Second reactor; 7. Second alkaline washing column; 8. Second drying column; 9. Third distillation column; and 10-21. Pipelines.

DETAILED DESCRIPTION OF THE EMBODIMENTS

For further illustrating the invention, experiments detailing a method for preparing 2,3,3,3-tetrafluoropropene are described below. It should be noted that the following examples are intended to describe and not to limit the invention.

As shown in the sole figure, raw materials hexafluoropropylene and $H_2$ are introduced to a first reactor for reaction to yield a mixture comprising 1,1,1,2,3,3-hexafluoropropane, 1,1,1,2,3-pentafluoropropene, HF, and HFP at an outlet of the first reactor. The mixture is introduced via a pipeline 10 to a first alkaline washing column 2 for removing HF therefrom. A resulting mixture is introduced to a first drying tower 3 via a pipeline 11 for drying, then to a first distillation column 4 via a pipeline 12. 1,1,1,2,3,3-hexafluoropropane is obtained at a bottom of the first distillation column 4 and cycled to the first reactor via a pipeline 13, and 1,1,1,2,3-pentafluoropropene and HFP are obtained at a top of the first distillation column 4 and introduced to a second distillation column 5 via a pipeline 14. HEP was obtained at a top of the second distillation column 5 and cycled to the first reactor via a pipeline 15; and 1,1,1,2,3-pentafluoropropene was obtained at a bottom of the second distillation column 5 and introduced to a second reactor via a pipe 16. In the meanwhile, fresh $H_2$ is added to the second reactor for reaction to yield a mixture comprising 1,1,1,2,3-pentafluoropropane, 2,3,3,3-tetrafluoropropene, HF, and $H_2$ at an outlet of the second reactor. The mixture is than introduced to a second alkaline washing column 7 via a pipe 17 for removing HF therefrom. A resulting mixture is introduced to a second drying column 8 via a pipe 18, and then to a third distillation column 9 via a pipe 19. 1,1,1,2,3-pentafluoropropane is obtained at a bottom of the third distillation column 9 and cycled to the second reactor via a pipe 20, product 2,3,3,3-tetrafluoropropene is obtained at a top of the third distillation column 9, and $H_2$ is discharged as a non-condensed gas.

Example 1

200 mL of a $Cr_2O_3$ catalyst was added with HF for fluorination at a temperature of 350° C. for 30 hrs to yield an activated $Cr_2O_3$ catalyst, which was then added to a lower section of the first reactor (adiabatic reactor made of carbon steel). 150 mL of a Pd/C catalyst (Pd accounts for 0.1 wt. %) was pretreated with a mixed gas comprising $H_2$ and $N_2$ (a molar ratio of $H_2$ to $N_2$ is 1:19) at a space velocity of 1200 mL $g^{-1}$ (catal.) $h^{-1}$ at a temperature of 350° C. for 15 hrs, then the Pd/C catalyst after treatment was filled in an upper section of the first reactor. The upper section of the first reactor was heated to a temperature of 50° C., and the lower section thereof was heated to the temperature of 300° C. Thereafter, hexafluoropropylene and $H_2$ with a molar ratio of 1:0.95 was introduced to the first reactor at a space velocity of 300 $h^{-1}$ for reaction, and products obtained from an outlet of the first reactor were washed by an alkaline and then samples were collected for analysis, results of which are listed in Table 1-1.

TABLE 1-1

Data analysis of organic substances at an outlet of a first reactor

| Components | 1,1,1,2,3-pentafluoropropene | 1,1,1,2,3,3-hexafluoropropane | HFP |
|---|---|---|---|
| Contents (wt. %) | 36.2 | 63.5 | 0.3 |

200 mL of a catalyst comprising $Cr_2O_3$ and $ZnO_2$ (90 wt. % of $Cr_2O_3$ and 10 wt. % of $ZnO_2$) was added with HF for fluorination at a temperature of 350° C. for 30 hrs to yield an activated catalyst comprising $Cr_2O_3$ and $ZnO_2$, which was then added to a lower section of the second reactor (adiabatic reactor made of carbon steel). 180 mL of a $Pd/Al_2O_3$ catalyst (Pd accounts for 0.3 wt. %) was pretreated with a mixed gas comprising $H_2$ and $N_2$ (a molar ratio of $H_2$ to $N_2$ is 1:19) at a space velocity of 1200 mL $g^{-1}$ (catal.) h at a temperature of 350° C. for 15 hrs, then the $Pd/Al_2O_3$ catalyst after treatment was filled in an upper section of the second reactor. The upper section of the second reactor was heated to a temperature of 100° C., and the lower section thereof was heated to the temperature of 320° C. Thereafter, 1,1,1,2,3-pentafluoropropene and $H_2$ obtained from the first reactor were introduced to the second reactor for reaction with a molar ratio of $H_2$ to 1,1,1,2,3-pentafluoropropene of 1:0.96 and a space velocity of 300 $h^{-1}$, and products obtained from an outlet of the second reactor were washed by an alkaline and then samples were collected for analysis, results of which are listed in Table 1-2.

TABLE 1-2

Data analysis of organic substances at an outlet of a second reactor

| Components | 2,3,3,3-tetrafluoropropene | 1,1,1,2,3-pentafluoropropane |
|---|---|---|
| Contents (wt. %) | 28.3 | 71.7 |

Example 2

The activation of the $Cr_2O_3$ catalyst and the pretreatment of the Pd/C catalyst were the same as Example 1. 200 mL of the activated $Cr_2O_3$ catalyst was filled in a lower section of a first reactor (adiabatic reactor made of carbon steel), and 150 mL of the pretreated Pd/C catalyst (Pd accounts for 0.3 wt. %) was filled in an upper section of the first reactor. The upper section of the first reactor was heated to the temperature of 80° C., and the lower section of the first reactor was heated to the temperature of 280° C. Hexafluoropropylene and $H_2$ were introduced to the first reactor at a molar ratio of hexafluoropropylene to $H_2$ of 1:0.95 at a space velocity of 200 $h^{-1}$ for reaction, and products obtained from an outlet of the first reactor were washed by an alkaline and then samples were collected for analysis, results of which are listed in Table 2-1.

TABLE 2-1

Data analysis of organic substances at an outlet of a first reactor

| Components | 1,1,1,2,3-pentafluoropropene | 1,1,1,2,3,3-hexafluoropropane | HFP |
|---|---|---|---|
| Contents (wt. %) | 42.5 | 57.3 | 0.2 |

The activation of the catalyst comprising $Cr_2O_3$ and $ZnO_2$ and the pretreatment of the $Pd/Al_2O_3$ catalyst were the same as Example 1. 200 mL of the activated catalyst comprising $Cr_2O_3$ and $ZnO_2$ (88 wt. % of $Cr_2O_3$ and 12 wt. % of $ZnO_2$) was filled in a lower section of the second reactor (adiabatic reactor made of carbon steel), and 180 mL of the pretreated $Pd/Al_2O_3$ catalyst (containing 0.5 wt. % of Pd) was filled in an upper section of the second reactor. The upper section of the second reactor was heated to the temperature of 120° C., and the lower section thereof was heated to the temperature of 300° C. Thereafter, 1,1,1,2,3-pentafluoropropene and $H_2$ obtained from the first reactor were introduced to the second reactor for reaction with a molar ratio of $H_2$ to 1,1,1,2,3-pentafluoropropene of 1:0.95 and a space velocity of 800 $h^{-1}$, and products obtained from an outlet of the second reactor were washed by an alkaline and then samples were collected for analysis, results of which are listed in Table 2-2.

TABLE 2-2

Data analysis of organic substances at an outlet of a second reactor

| Components | 2,3,3,3-tetrafluoropropene | 1,1,1,2,3-pentafluoropropane |
|---|---|---|
| Contents (wt. %) | 31.7 | 68.3 |

Example 3

The activation of the $Cr_2O_3$ catalyst and the pretreatment of the Pd/C catalyst were the same as Example 1. 200 mL of the activated $Cr_2O_3$ catalyst was filled in a lower section of a first reactor (adiabatic reactor made of carbon steel), and 150 mL of the pretreated Pd/C catalyst (containing 0.5 wt. % of Pd) was filled in an upper section of the first reactor. The upper section of the first reactor was heated to the temperature of 100° C., and the lower section of the first reactor was heated to the temperature of 320° C. Hexafluoropropylene and $H_2$ were introduced to the first reactor at a molar ratio of hexafluoropropylene to $H_2$ of 1:0.97 at a space velocity of 800 $h^{-1}$ for reaction, and products obtained from an outlet of the first reactor were washed by an alkaline and then samples were collected for analysis, results of which are listed in Table 3-1.

TABLE 3-1

Data analysis of organic substances at an outlet of a first reactor

| Components | 1,1,1,2,3-pentafluoropropene | 1,1,1,2,3,3-hexafluoropropane | HFP |
|---|---|---|---|
| Contents (wt. %) | 54.3 | 45.6 | 0.1 |

The activation of the catalyst comprising $Cr_2O_3$ and $ZnO_2$ and the pretreatment of the $Pd/Al_2O_3$ catalyst were the same as Example 1. 200 mL of the activated catalyst comprising $Cr_2O_3$ and $ZnO_2$ (88 wt. % of $Cr_2O_3$ and 12 wt. % of $ZnO_2$) was filled in a lower section of the second reactor (adiabatic reactor made of carbon steel), and 180 mL of the pretreated $Pd/Al_2O_3$ catalyst (containing 0.8 wt. % of Pd) was filled in an upper section of the second reactor. The upper section of the second reactor was heated to the temperature of 150° C., and the lower section thereof was heated to the temperature of 400° C. Thereafter, 1,1,1,2,3-pentafluoropropene and $H_2$ obtained from the first reactor were introduced to the second reactor for reaction with a molar ratio of $H_2$ to 1,1,1,2,3-pentafluoropropene of 1:0.97 and a space velocity of 800 $h^{-1}$, and products obtained from an outlet of the second reactor were washed by an alkaline and then samples were collected for analysis, results of which are listed in Table 3-2.

TABLE 3-2

Data analysis of organic substances at an outlet of a second reactor

| Components | 2,3,3,3-tetrafluoropropene | 1,1,1,2,3-pentafluoropropane |
|---|---|---|
| Contents (wt. %) | 56.8 | 43.2 |

Example 4

The activation of the $Cr_2O_3$ catalyst and the pretreatment of the Pd/C catalyst were the same as Example 1. 200 mL of the activated $Cr_2O_3$ catalyst was filled in a lower section of a first reactor (adiabatic reactor made of carbon steel), and 150 mL of the pretreated Pd/C catalyst (containing 0.8 wt. % of Pd) was filled in an upper section of the first reactor. The upper section of the first reactor was heated to the temperature of 120° C., and the lower section of the first reactor was heated to the temperature of 310° C. Hexafluoropropylene and $H_2$ were introduced to the first reactor at a molar ratio of hexafluoropropylene to $H_2$ of 1:0.97 at a space velocity of 600 $h^{-1}$ for reaction, and products obtained from an outlet of the first reactor were washed by an alkaline and then samples were collected for analysis, results of which are listed in Table 4-1.

TABLE 4-1

Data analysis of organic substances at an outlet of a first reactor

| Components | 1,1,1,2,3-pentafluoropropene | 1,1,1,2,3,3-hexafluoropropane | HFP |
|---|---|---|---|
| Contents (wt. %) | 57 | 42.8 | 0.2 |

The activation of the catalyst comprising $Cr_2O_3$ and $ZnO_2$ and the pretreatment of the $Pd/Al_2O_3$ catalyst were the same as Example 1. 200 mL of the activated catalyst comprising $Cr_2O_3$ and $ZnO_2$ (88 wt. % of $Cr_2O_3$ and 12 wt. % of $ZnO_2$) was filled in a lower section of the second reactor (adiabatic reactor made of stainless steel), and 180 mL of the pretreated $Pd/Al_2O_3$ catalyst (containing 1.5 wt. % of Pd) was filled in an upper section of the second reactor. The upper section of the second reactor was heated to the temperature of 130° C., and the lower section thereof was heated to the temperature of 350° C. Thereafter, 1,1,1,2,3-pentafluoropropene and $H_2$ obtained from the first reactor were introduced to the second reactor for reaction with a molar ratio of $H_2$ to 1,1,1,2,3-pentafluoropropene of 1:0.97 and a space velocity of 1000 $h^{-1}$, and products obtained from an outlet of the second reactor were washed by an alkaline and then samples were collected for analysis, results of which are listed in Table 4-2.

TABLE 4-2

Data analysis of organic substances at an outlet of a second reactor

| Components | 2,3,3,3-tetrafluoropropene | 1,1,1,2,3-pentafluoropropane |
|---|---|---|
| Contents (wt. %) | 61.5 | 38.5 |

Example 5

The activation of the $Cr_2O_3$ catalyst and the pretreatment of the Pd/C catalyst were the same as Example 1. 200 mL of the activated $Cr_2O_3$ catalyst was filled in a lower section of a first reactor (adiabatic reactor made of carbon steel), and 150 mL of the pretreated Pd/C catalyst (containing 1.0 wt. % of Pd) was filled in an upper section of the first reactor. The upper section of the first reactor was heated to the temperature of 150° C., and the lower section of the first reactor was heated to the temperature of 330° C. Hexafluoropropylene and $H_2$ were introduced to the first reactor at a molar ratio of hexafluoropropylene to $H_2$ of 1:0.98 at a space velocity of 1000 $h^{-1}$ for reaction, and products obtained from an outlet of the first reactor were washed by an alkaline and then samples were collected for analysis, results of which are listed in Table 5-1.

TABLE 5-1

Data analysis of organic substances at an outlet of a first reactor

| Components | 1,1,1,2,3-pentafluoropropene | 1,1,1,2,3,3-hexafluoropropane | HFP |
|---|---|---|---|
| Contents (wt. %) | 68.4 | 31.5 | 0.1 |

The activation of the catalyst comprising $Cr_2O_3$ and $ZnO_2$ and the pretreatment of the $Pd/Al_2O_3$ catalyst were the same as Example 1. 200 mL of the activated catalyst comprising $Cr_2O_3$ and $ZnO_2$ (90 wt. % of $Cr_2O_3$ and 10 wt. % of $ZnO_2$) was filled in a lower section of the second reactor (adiabatic reactor made of stainless steel), and 180 mL of the pretreated $Pd/Al_2O_3$ catalyst (containing 0.5 wt. % of Pd) was filled in an upper section of the second reactor. The upper section of the second reactor was heated to the temperature of 100° C., and the lower section thereof was heated to the temperature of 450° C. Thereafter, 1,1,1,2,3-pentafluoropropene and $H_2$ obtained from the first reactor were introduced to the second reactor for reaction with a molar ratio of $H_2$ to 1,1,1,2,3-pentafluoropropene of 1:0.98 and a space velocity of 1500 $h^{-1}$, and products obtained from an outlet of the second reactor were washed by an alkaline and then samples were collected for analysis, results of which are listed in Table 5-2.

TABLE 5-2

Data analysis of organic substances at an outlet of a second reactor

| Components | 2,3,3,3-tetrafluoropropene | 1,1,1,2,3-pentafluoropropane |
|---|---|---|
| Contents (wt. %) | 79.7 | 20.3 |

Example 6

The activation of the $Cr_2O_3$ catalyst and the pretreatment of the Pd/C catalyst were the same as Example 1. 200 mL of the activated $Cr_2O_3$ catalyst was filled in a lower section of a first reactor (adiabatic reactor made of carbon steel), and 150 mL of the pretreated Pd/C catalyst (containing 1.0 wt. % of Pd) was filled in an upper section of the first reactor. The upper section of the first reactor was heated to the temperature of 130° C., and the lower section of the first reactor was heated to the temperature of 400° C. Hexafluoropropylene and $H_2$ were introduced to the first reactor at a molar ratio of hexafluoropropylene to $H_2$ of 1:0.98 at a space velocity of 500 $h^{-1}$ for reaction, and products obtained from an outlet of the first reactor were washed by an alkaline and then samples were collected for analysis, results of which are listed in Table 6-1.

TABLE 6-1

Data analysis of organic substances at an outlet of a first reactor

| Components | 1,1,1,2,3-pentafluoropropene | 1,1,1,2,3,3-hexafluoropropane | HFP |
|---|---|---|---|
| Contents (wt. %) | 74.4 | 25.4 | 0.2 |

The activation of the catalyst comprising $Cr_2O_3$ and $ZnO_2$ and the pretreatment of the $Pd/Al_2O_3$ catalyst were the same as Example 1. 200 mL of the activated catalyst comprising $Cr_2O_3$ and $ZnO_2$ (80 wt. % of $Cr_2O_3$ and 20 wt. % of $ZnO_2$) was filled in a lower section of the second reactor (adiabatic reactor made of stainless steel), and 180 mL of the pretreated $Pd/Al_2O_3$ catalyst (containing 0.3 wt. % of Pd) was filled in an upper section of the second reactor. The upper section of the second reactor was heated to the temperature of 100° C., and the lower section thereof was heated to the temperature of 500° C. Thereafter, 1,1,1,2,3-pentafluoropropene and $H_2$ obtained from the first reactor were introduced to the second reactor for reaction with a molar ratio of $H_2$ to 1,1,1,2,3-pentafluoropropene of 1:0.95 and a space velocity of 2000 $h^{-1}$, and products obtained from an outlet of the second reactor were washed by an alkaline and then samples were collected for analysis, results of which are listed in Table 6-2.

TABLE 6-2

Data analysis of organic substances at an outlet of a second reactor

| Components | 2,3,3,3-tetrafluoropropene | 1,1,1,2,3-pentafluoropropane |
|---|---|---|
| Contents (wt. %) | 84.6 | 15.4 |

Example 7

The activation of the $Cr_2O_3$ catalyst and the pretreatment of the Pd/C catalyst were the same as Example 1. 200 mL of the activated $Cr_2O_3$ catalyst was filled in a lower section of a first reactor (adiabatic reactor made of carbon steel), and 150 mL of the pretreated Pd/C catalyst (containing 0.3 wt. % of Pd) was filled in an upper section of the first reactor. The upper section of the first reactor was heated to the temperature of 100° C., and the lower section of the first reactor was heated to the temperature of 300° C. Hexafluoropropylene and $H_2$ were introduced to the first reactor at a molar ratio of hexafluoropropylene to $H_2$ of 1:0.99 at a space velocity of 300 $h^{-1}$ for reaction, and products obtained from an outlet of the first reactor were washed by an alkaline and then samples were collected for analysis, results of which are listed in Table 7-1.

TABLE 7-1

Data analysis of organic substances at an outlet of a first reactor

| Components | 1,1,1,2,3-pentafluoropropene | 1,1,1,2,3,3-hexafluoropropane | HFP |
|---|---|---|---|
| Contents (wt. %) | 61.4 | 38.5 | 0.1 |

The activation of the catalyst comprising $Cr_2O_3$ and $ZnO_2$ and the pretreatment of the $Pd/Al_2O_3$ catalyst were the same as Example 1. 200 mL of the activated catalyst comprising $Cr_2O_3$ and $ZnO_2$ (90 wt. % of $Cr_2O_3$ and 10 wt. % of $ZnO_2$) was filled in a lower section of the second reactor (adiabatic reactor made of stainless steel), and 180 mL of the pretreated $Pd/Al_2O_3$ catalyst (containing 0.5 wt. % of Pd) was filled in an upper section of the second reactor. The upper section of the second reactor was heated to the temperature of 150° C., and the lower section thereof was heated to the temperature of 300° C. Thereafter, 1,1,1,2,3-pentafluoropropene and $H_2$ obtained from the first reactor were introduced to the second reactor for reaction with a molar ratio of $H_2$ to 1,1,1,2,3-pentafluoropropene of 1:0.99 and a space velocity of 600 $h^{-1}$, and products obtained from an outlet of the second reactor were washed by an alkaline and then samples were collected for analysis, results of which are listed in Table 7-2.

TABLE 7-2

Data analysis of organic substances at an outlet of a second reactor

| Components | 2,3,3,3-tetrafluoropropene | 1,1,1,2,3-pentafluoropropane |
|---|---|---|
| Contents (wt. %) | 62.4 | 37.6 |

Example 8

The activation of the $Cr_2O_3$ catalyst and the pretreatment of the Pd/C catalyst were the same as Example 1. 200 mL of the activated $Cr_2O_3$ catalyst was filled in a lower section of a first reactor (adiabatic reactor made of carbon steel), and 150 mL of the pretreated Pd/C catalyst (containing 0.3 wt. % of Pd) was filled in an upper section of the first reactor. The upper section of the first reactor was heated to the temperature of 120° C., and the lower section of the first reactor was heated to the temperature of 250° C. Hexafluoropropylene and $H_2$ were introduced to the first reactor at a molar ratio of hexafluoropropylene to $H_2$ of 1:0.99 at a space velocity of 500 h$^{-1}$ for reaction, and products obtained from an outlet of the first reactor were washed by an alkaline and then samples were collected for analysis, results of which are listed in Table 8-1.

TABLE 8-1

Data analysis of organic substances at an outlet of a first reactor

| Components | 1,1,1,2,3-pentafluoropropene | 1,1,1,2,3,3-hexafluoropropane | HFP |
|---|---|---|---|
| Contents (wt. %) | 52.7 | 47.2 | 0.1 |

The activation of the catalyst comprising $Cr_2O_3$ and $ZnO_2$ and the pretreatment of the Pd/$Al_2O_3$ catalyst were the same as Example 1. 200 mL of the activated catalyst comprising $Cr_2O_3$ and $ZnO_2$ (90 wt. % of $Cr_2O_3$ and 10 wt. % of $ZnO_2$) was filled in a lower section of the second reactor (adiabatic reactor made of stainless steel), and 180 mL of the pretreated Pd/$Al_2O_3$ catalyst (containing 0.3 wt. % of Pd) was filled in an upper section of the second reactor. The upper section of the second reactor was heated to the temperature of 150° C., and the lower section thereof was heated to the temperature of 300° C. Thereafter, 1,1,1,2,3-pentafluoropropene and $H_2$ obtained from the first reactor were introduced to the second reactor for reaction with a molar ratio of $H_2$ to 1,1,1,2,3-pentafluoropropene of 1:0.95 and a space velocity of 600 h$^{-1}$, and products obtained from an outlet of the second reactor were washed by an alkaline and then samples were collected for analysis, results of which are listed in Table 8-2.

TABLE 8-2

Data analysis of organic substances at an outlet of a second reactor

| Components | 2,3,3,3-tetrafluoropropene | 1,1,1,2,3-pentafluoropropane |
|---|---|---|
| Contents (wt. %) | 56.7 | 43.3 |

Example 9

The activation of the $Cr_2O_3$ catalyst and the pretreatment of the Pd/C catalyst were the same as Example 1. 200 mL of the activated $Cr_2O_3$ catalyst was filled in a lower section of a first reactor (adiabatic reactor made of carbon steel), and 150 mL of the pretreated Pd/C catalyst (containing 0.3 wt. % of Pd) was filled in an upper section of the first reactor. The upper section of the first reactor was heated to the temperature of 80° C., and the lower section of the first reactor was heated to the temperature of 320° C. Hexafluoropropylene and $H_2$ were introduced to the first reactor at a molar ratio of hexafluoropropylene to $H_2$ of 1:0.99 at a space velocity of 500 h$^{-1}$ for reaction, and products obtained from an outlet of the first reactor were washed by an alkaline and then samples were collected for analysis, results of which are listed in Table 9-1.

TABLE 9-1

Data analysis of organic substances at an outlet of a first reactor

| Components | 1,1,1,2,3-pentafluoropropene | 1,1,1,2,3,3-hexafluoropropane | HFP |
|---|---|---|---|
| Contents (wt. %) | 64.1 | 35.8 | 0.1 |

The activation of the catalyst comprising $Cr_2O_3$ and $ZnO_2$ and the pretreatment of the Pd/$Al_2O_3$ catalyst were the same as Example 1. 200 mL of the activated catalyst comprising $Cr_2O_3$ and $ZnO_2$ (90 wt. % of $Cr_2O_3$ and 10 wt. % of $ZnO_2$) was filled in a lower section of the second reactor (adiabatic reactor made of stainless steel), and 180 mL of the pretreated Pd/$Al_2O_3$ catalyst (containing 0.5 wt. % of Pd) was filled in an upper section of the second reactor. The upper section of the second reactor was heated to the temperature of 100° C., and the lower section thereof was heated to the temperature of 350° C. Thereafter, 1,1,1,2,3-pentafluoropropene and $H_2$ obtained from the first reactor were introduced to the second reactor for reaction with a molar ratio of $H_2$ to 1,1,1,2,3-pentafluoropropene of 1:0.95 and a space velocity of 400 h$^{-1}$, and products obtained from an outlet of the second reactor were washed by an alkaline and then samples were collected for analysis, results of which are listed in Table 9-2.

TABLE 9-2

Data analysis of organic substances at an outlet of a second reactor

| Components | 2,3,3,3-tetrafluoropropene | 1,1,1,2,3-pentafluoropropane |
|---|---|---|
| Contents (wt. %) | 58.4 | 41.6 |

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for preparing 2,3,3,3-tetrafluoropropene, comprising:
   a) introducing hexafluoropropylene and hydrogen to a first reactor to allow hexafluoropropylene to react with hydrogen in the presence of a catalyst to obtain a first mixture comprising 1,1,1,2,3-pentafluoropropene, 1,1,1,2,3,3-hexafluoropropane, hydrogen fluoride, and hexafluoropropylene, in which a molar ratio of hexafluoropropylene to hydrogen is between 1:0.95 and 1:0.99, a space velocity is between 200 and 1000 h$^{-1}$, and a reaction temperature is between 50 and 400° C.;
   b) washing and drying the first mixture obtained from a), and introducing the treated first mixture to a first distillation column to obtain 1,1,1,2,3,3-hexafluoropropane in a bottom of the first distillation column and 1,1,1,2,3-pentafluoropropene and hexafluoropropylene at a top of the first distillation column; recycling the 1,1,1,2,3,3-hexafluoropropane to the first reactor, and introducing the 1,1,1,2,3-pentafluoropropene and the hexafluoropropylene to a second distillation column to yield hexafluoropropylene at a top of the second distillation column and 1,1,1,2,3-pentafluoropropene at a bottom the second distillation column; and recycling the hexafluoropropylene to the first reactor;

c) introducing the 1,1,1,2,3-pentafluoropropene obtained from b) and hydrogen to a second reactor and allowing the 1,1,1,2,3-pentafluoropropene to react with the hydrogen in the presence of a catalyst, to obtain a second mixture comprising 1,1,1,2,3-pentafluoropropane, 2,3,3,3-tetrafluoropropene, HF, and H2, in which a molar ratio of the hydrogen to the 1,1,1,2,3-pentafluoropropene is between 1:0.95 and 1:0.99, a space velocity is between 300 and 2000 h−1, and a reaction temperature is between 80 and 500° C.; and d) washing and drying the second mixture obtained from c), and introducing the second mixture to a third distillation column to yield 1,1,1,2,3-pentafluoropropane at a bottom of the third distillation column; and recycling the 1,1,1,2,3-pentafluoropropane to the second reactor, to yield 2,3,3,3-tetrafluoropropene at a top of third distillation column.

2. The method of claim 1, wherein the space velocity in a) is between 400 and 800 h$^{-1}$, and the reaction temperature is between 100 and 300° C.

3. The method of claim 1, wherein the space velocity in c) is between 600 and 1500 h$^{-1}$, and the reaction temperature is between 120 and 400° C.

4. The method of claim 1, wherein
the catalyst in the first reactor is respectively filled in an upper section and a lower section of the first reactor;
the catalyst in the upper section of the first reactor is Pd/C, and Pd accounts for between 0.1 and 1 wt. %; and
the catalyst in the lower section of the first reactor is chromium oxide.

5. The method of claim 1, wherein
the catalyst in the second reactor is respectively filled in an upper section and a lower section of the second reactor;
the catalyst in the upper section of the second reactor is Pd/Al2O3, and Pd accounts for between 0.2 and 1.5 wt. %; and
the catalyst in the lower section of the second reactor comprises between 80 and 90 wt. % of chromium oxide and between 10 and 20 wt. % of zinc oxide.

6. The method of claim 1, wherein both the first reactor and the second reactor are adiabatic reactors.

* * * * *